(12) United States Patent
Davis et al.

(10) Patent No.: US 7,935,497 B2
(45) Date of Patent: May 3, 2011

(54) PROTEASE DETECTION

(75) Inventors: Paul James Davis, Felmersham (GB);
Mark James Davis, Souldrop (GB);
Mark Burnapp, Bedford (GB)

(73) Assignee: Mologic Ltd, Bedfordshire (GB)

( * ) Notice: Subject to any disclaimer, the term of this patent is extended or adjusted under 35 U.S.C. 154(b) by 203 days.

(21) Appl. No.: 12/280,383

(22) PCT Filed: Feb. 23, 2007

(86) PCT No.: PCT/GB2007/000637
§ 371 (c)(1), (2), (4) Date: Nov. 6, 2008

(87) PCT Pub. No.: WO2007/096637
PCT Pub. Date: Aug. 30, 2007

(65) Prior Publication Data
US 2009/0053738 A1    Feb. 26, 2009

(30) Foreign Application Priority Data
Feb. 23, 2006  (GB) .................................. 0603665.1

(51) Int. Cl.
G01N 33/53    (2006.01)
(52) U.S. Cl. ........................ 435/7.4; 435/7.95; 435/7.93
(58) Field of Classification Search .................. 436/514, 436/518; 435/7.1, 7.91, 7.94
See application file for complete search history.

(56) References Cited

U.S. PATENT DOCUMENTS

| | | |
|---|---|---|
| 3,888,629 A | 6/1975 | Bagshawe |
| 4,055,394 A | 10/1977 | Friedman |
| 4,144,306 A | 3/1979 | Figueras et al. |
| 4,178,153 A | 12/1979 | Sodickson et al. |
| 4,258,001 A | 3/1981 | Pierce et al. |
| 4,356,149 A | 10/1982 | Kitajima et al. |
| 4,522,923 A | 6/1985 | Deutsch |
| 4,604,264 A | 8/1986 | Rothe et al. |
| 4,689,240 A | 8/1987 | Zweig |
| 4,703,017 A | 10/1987 | Campbell et al. |
| 4,727,019 A | 2/1988 | Valkirs et al. |
| 4,820,489 A | 4/1989 | Rothe et al. |
| 4,851,356 A | 7/1989 | Canfield |
| 4,870,005 A | 9/1989 | Akiyoshi et al. |
| 4,952,520 A | 8/1990 | Okusa et al. |
| 5,064,770 A | 11/1991 | DeLuca et al. |
| 5,071,746 A | 12/1991 | Wilk et al. |
| 5,171,662 A | 12/1992 | Sharma |
| 5,185,249 A | 2/1993 | Arter et al. |
| 5,236,826 A | 8/1993 | Marshall |
| 5,284,622 A | 2/1994 | Krause et al. |
| 5,296,192 A | 3/1994 | Carroll et al. |
| 5,565,366 A | 10/1996 | Akers, Jr. |
| 5,601,986 A | 2/1997 | Takacs |
| 5,629,164 A | 5/1997 | Rivers |
| 5,741,659 A | 4/1998 | Ralls et al. |
| 5,755,231 A | 5/1998 | Krantz et al. |
| 5,766,961 A | 6/1998 | Pawlak et al. |
| 5,879,881 A | 3/1999 | Rubenstein |
| 5,932,410 A | 8/1999 | Whittaker et al. |
| 6,040,195 A | 3/2000 | Carroll et al. |
| 6,096,563 A | 8/2000 | Hajizadeh et al. |
| 6,352,862 B1 | 3/2002 | Davis et al. |
| 6,686,170 B1 | 2/2004 | Flanders et al. |
| 6,750,034 B1 | 6/2004 | Darrow et al. |
| 2003/0207290 A1 | 11/2003 | Kenten et al. |
| 2003/0211560 A1 | 11/2003 | O'Brien et al. |
| 2003/0219833 A1 | 11/2003 | Guan et al. |
| 2004/0029176 A1 | 2/2004 | Yoon |
| 2004/0038217 A1 | 2/2004 | Yang |
| 2004/0067168 A1 | 4/2004 | Buffiere et al. |
| 2004/0096926 A1 | 5/2004 | Packard et al. |
| 2004/0236555 A1 * | 11/2004 | Pierce et al. .................... 703/11 |
| 2005/0164311 A1 | 7/2005 | Inglese et al. |
| 2006/0003394 A1 | 1/2006 | Song |
| 2006/0234284 A1 | 10/2006 | Yang |

FOREIGN PATENT DOCUMENTS

| | | |
|---|---|---|
| CA | 2569487 A1 | 12/2005 |
| EP | 0339450 A2 | 11/1989 |
| EP | 0206075 B1 | 12/1989 |
| EP | 0158964 B1 | 11/1990 |
| EP | 0450714 A2 | 10/1991 |
| EP | 0579250 A2 | 1/1994 |
| EP | 1394270 A2 | 3/2004 |
| EP | 2004845 A1 | 7/2004 |
| EP | 1986779 A1 | 11/2008 |
| EP | 1989549 A1 | 11/2008 |
| EP | 1991870 A1 | 11/2008 |
| FR | 2621393 A1 | 4/1989 |
| GB | 2259362 A | 3/1993 |
| GB | 2342993 A | 4/2000 |
| GB | 2 350 677 | 12/2000 |
| GB | 2410086 A | 7/2005 |
| JP | 57064160 A | 4/1982 |
| JP | 2001000197 A | 1/2001 |

(Continued)

OTHER PUBLICATIONS

U.S. Appl. No. 12/280,245, filed Nov. 6, 2008, Davis et al.
U.S. Appl. No. 12/280,290, filed Aug. 21, 2008, Davis et al.
U.S. Appl. No. 12/296,413, filed Oct. 7, 2008, Davis et al.
Anonymous, Quick-StepTM HCG—One Step Urine Pregnancy Test, Internet Citation, XP002423569, 1998.
Secchi et al., "Monoclonal Antibody Capture Fluorometric Enzyme Linked Immunosorbent Assay for Detection of Porcine Growth Hormone in Plasma," Analytica Chimica Acta 402:37-45, 1999.
International Search Report (PCT/GB2007/000641) mailed Jun. 5, 2007.
International Search Report (PCT/GB2007/000643) mailed Jun. 1, 2007.
International Search Report (PCT/GB2007/001291) mailed Sep. 14, 2007.
International Preliminary Report on Patentability (PCT/GB2007/000641) mailed Sep. 4, 2008.

(Continued)

Primary Examiner — Bao-Thuy L Nguyen
(74) Attorney, Agent, or Firm — Clark & Elbing LLP

(57) ABSTRACT

A method of detecting a protease in a sample. The method comprises providing an analyte degradable by the protease. The analyte is contacted with the sample. The degradation products of the analyte or the residual undegraded analyte is detected in a binding assay.

8 Claims, 5 Drawing Sheets

FOREIGN PATENT DOCUMENTS

| | | | |
|---|---|---|---|
| WO | WO 88/08534 | * | 11/1988 |
| WO | WO 89/10564 | A1 | 11/1989 |
| WO | WO 91/14000 | A1 | 9/1991 |
| WO | WO 92/15879 | A1 | 9/1992 |
| WO | WO 96/30751 | A1 | 10/1996 |
| WO | WO 96/38727 | A1 | 12/1996 |
| WO | WO 98/00703 | A1 | 1/1998 |
| WO | WO 98/33069 | A1 | 7/1998 |
| WO | WO 98/50778 | A1 | 11/1998 |
| WO | WO 99/67647 | A1 | 12/1999 |
| WO | WO 00/62061 | A1 | 10/2000 |
| WO | WO 00/63700 | A1 | 10/2000 |
| WO | WO 01/25789 | A1 | 4/2001 |
| WO | WO 01/31337 | A2 | 5/2001 |
| WO | WO 02/35216 | A1 | 5/2002 |
| WO | WO 02/42770 | | 5/2002 |
| WO | WO 02/48674 | A2 | 6/2002 |
| WO | WO 03/012443 | A2 | 2/2003 |
| WO | WO 03/058252 | A2 | 7/2003 |
| WO | WO 2004/048935 | A3 | 6/2004 |
| WO | WO 2004/103939 | A1 | 12/2004 |
| WO | WO 2005/005657 | A1 | 1/2005 |
| WO | WO 2005/012558 | A1 | 2/2005 |
| WO | WO 2005/119253 | A1 | 12/2005 |
| WO | WO 2006/006961 | A1 | 1/2006 |
| WO | WO 2007/096637 | A1 | 8/2007 |
| WO | WO 2007/096640 | A1 | 8/2007 |
| WO | WO 2007/096642 | A1 | 8/2007 |
| WO | WO 2007/128980 | A1 | 11/2007 |

OTHER PUBLICATIONS

International Preliminary Report on Patentability (PCT/GB2007/000643) issued Aug. 26, 2008.
International Preliminary Report on Patentability (PCT/GB2007/001291) issued Oct. 8, 2008.
Written Opinion of the International Searching Authority (PCT/GB2007/000637) completed May 16, 2007.
Written Opinion of the International Searching Authority (PCT/GB2007/000641) completed May 16, 2007.
Written Opinion of the International Searching Authority (PCT/GB2007/000643) completed May 24, 2007.
Written Opinion of the International Searching Authority (PCT/GB2007/001291) completed Aug. 28, 2007.
International Search Report (PCT/GB2007/000637) mailed May 25, 2007.
International Preliminary Report on Patentability (PCT/GB2007/000637) mailed Sep. 4, 2008.
Communication in European Patent Application No. 07705268.6-2404 (May 29, 2009).
Response to Communication in European Patent Application No. 07705268.6 (Sep. 11, 2009).
Communication in European Patent Application No. 07705268.6-2404 (Mar. 31, 2010).
Response to Communication in European Patent Application No. 07705268.6 (Aug. 9, 2010).

* cited by examiner

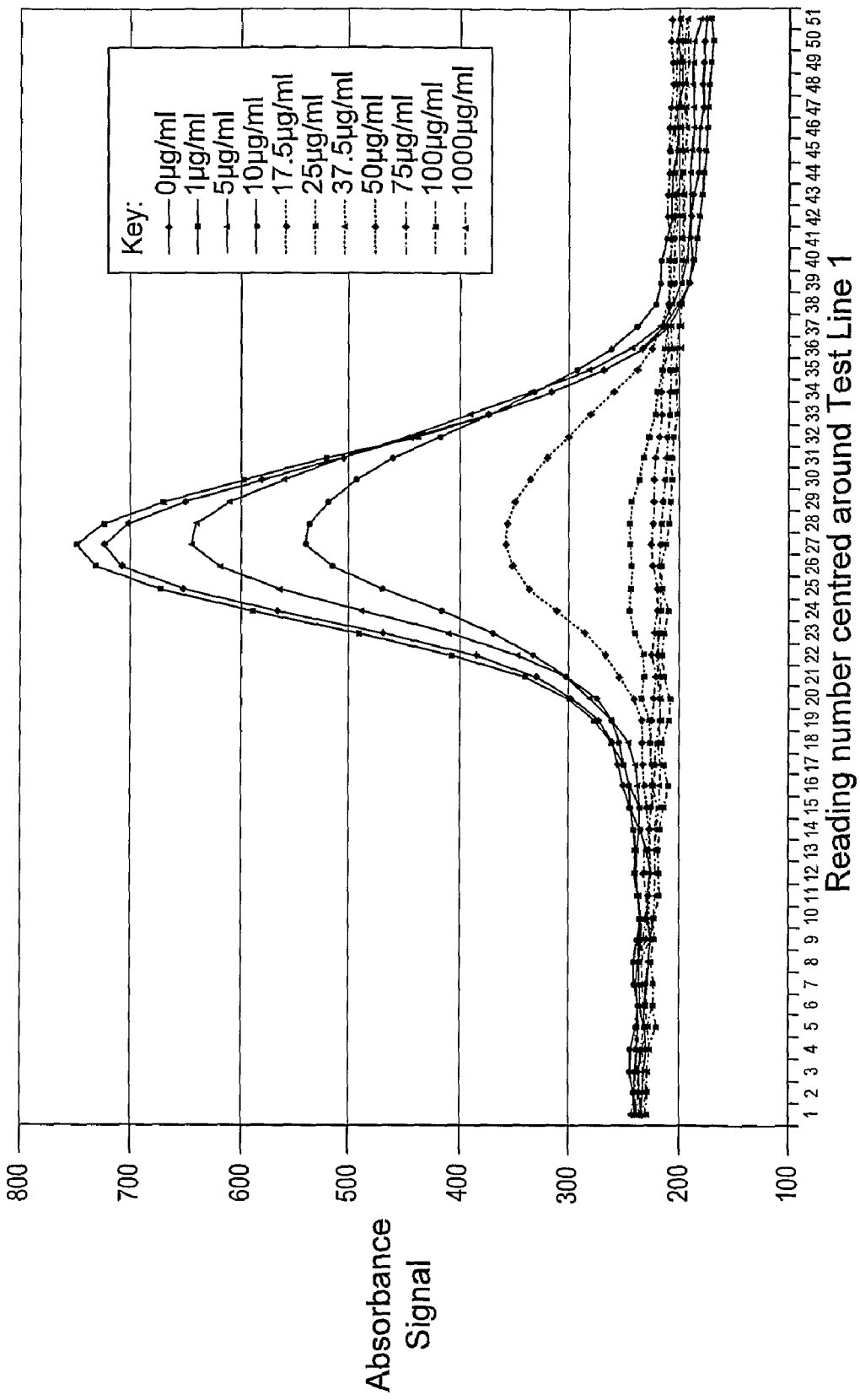

PROTEASE DETECTION

CROSS-REFERENCE TO RELATED APPLICATIONS

This application is the U.S. National Stage of International Application No. PCT/GB2007/000637, filed Feb. 23, 2007, which claims the benefit of 0603665.1, filed Feb. 23, 2006.

The present invention relates to a method of detecting a protease.

Proteases are enzymes which digest proteins, in particular by hydrolysing and cleaving peptide bonds. Thus, a protein which is degraded by a protease is cleaved into two or more smaller peptides. Some proteases will hydrolyse a peptide bond which is adjacent to a specific series of amino acid residues, whereas others are less specific, requiring only one or two specific amino acids to guide cleavage (e.g. Trypsin).

An entirely separate area of development has been that of lateral flow immunoassays. These immunoassays allow the detection of analytes in complex samples. A common example of such an immunoassay is a urine pregnancy testing kit, a prior art version of which is shown in FIG. 1.

Referring to FIG. 1, the kit 1 comprises a strip 2 made of nitrocellulose. At one end of the strip 2 is provided a sample receiving zone 3 which is made from an absorbent material. Further along the sample receiving zone 3 is provided a labelled antibody band 4 which is arranged transverse to the long axis of the strip 2. The labelled antibody band 4 comprises a plurality of monoclonal antibodies specific to human chorionic gonadotropin (hCG). Conjugated to each antibody is a gold particle. The antibodies in the labelled antibody band 4 can be rendered mobile by the passage of sample through the receiving zone 3, from the stable dried state.

Further along the strip 2, away from the sample receiving zone 3, is provided a capture antibody band 5 which is also arranged transverse to the long axis of the strip. The capture antibody band 5 comprises a plurality of monoclonal antibodies specific to a different epitope of hCG from the antibodies in the labelled antibody band 4. The antibodies in the capture antibody band are immobilised onto the nitrocellulose strip 2.

Further still along the strip 2, away from the sample receiving zone 3, and adjacent to the other end of the strip 2 is provided a control band 6 which is also arranged transverse to the long axis of the strip. The control band 6 comprises a plurality of antibodies, specific for species IgG. The antibodies in the control band are also immobilised onto the strip 2.

In order to use the kit 1, to test for pregnancy in an individual, a sample (typically urine) from the individual is deposited on the sample receiving zone 3. The sample naturally flows (following capillary force) along the length of the strip towards firstly the labelled antibody band 4, then the capture antibody band 5 and finally the control band 6 (i.e. in the direction of the arrow 7). It is to be appreciated that the strip 2 thus provides a liquid flow path for the sample.

As the contents of the sample pass the labelled antibody band 4, the labelled antibody is mobilised within the strip 2 and is also carried in the direction of the arrow 7. If hCG is present in the sample then the labelled antibody binds to the hCG.

When the labelled antibody reaches the capture antibody band 5, one of two things may happen. If hCG is present in the sample then the hCG binds to the capture antibodies. The majority of the hCG will already be bound to the labelled antibodies and thus a complex forms of the immobilised capture antibody, the hCG and the labelled antibody, the hCG forming a link or bridge between the capture antibody and the labelled antibody. Alternatively, if there is no hCG in the sample then the labelled antibody passes through the capture antibody band, without interacting with the capture antibodies. It is to be appreciated that the capture antibodies are immobilised and so in either case they do not flow along the strip 2.

Subsequently, the sample reaches the control band 6. In practice, even if hCG is present in the sample, there is sufficient labelled antibody present in the kit to ensure some material passes beyond the capture antibody band 5. Thus, whether or not hCG is present in the antibody, some labelled antibody reaches the control band 6. At the control band 6, the immobilised anti-IgG antibody binds to, and thus immobilises, the labelled antibody.

It is to be understood that where the labelled antibody is immobilised and concentrated, the presence of the gold particles forms a visible line. Thus, if hCG is present in the sample (which will be the case if the individual is pregnant) then a visible line forms at the capture antibody band 5. Whether or not hCG is present in the sample, a visible line will form at the control band 6. The line at the control band 6 is useful because it is indicative that the assay has reached its conclusion (which may not occur if, for example, there is insufficient liquid in the sample) and confirms the device has functioned correctly. It also permits a comparison of the capture antibody band 5 with the control band 6 in order to provide additional certainty of the result.

The present invention seeks to provide alternative methods of determining the presence of a protease.

According to one aspect of the present invention, there is provided a method of detecting a protease in a sample comprising the steps of:

(i) providing an analyte degradable by the protease;
(ii) contacting the analyte with the sample; and
(iii) detecting the degradation products of the analyte or the residual undegraded analyte in a binding assay.

Conveniently, the binding assay is a lateral flow assay.

Preferably, the binding assay is an immunoassay.

Advantageously, step (iii) comprises detecting the undegraded analyte.

Conveniently, the analyte is hCG.

According to another aspect of the present invention, there is provided a protease detection kit for detecting a protease enzyme in a sample comprising:

a supply of a protease sensitive analyte in isolated form;
a labelling component capable of binding to the analyte or a proteolytic fragment thereof, the labelling component being associatable with a label;
a capture component capable of binding to the analyte or a proteolytic fragment thereof; and
immobilising means for immobilising the capture component.

Conveniently, the protease detection kit further comprises a liquid flow path for the sample, the labelling component and the capture component being located on different portions of the liquid flow path.

Preferably, the protease detection kit further comprises a solid substrate, on which at least the capture component is located.

Advantageously, the capture component is immobilised on the solid substrate.

Conveniently, the labelling component and/or the capture component are antibodies or antigen binding fragments thereof.

In order that the present invention may be more fully understood and so that further embodiments thereof may be appreciated, the invention will now be described by way of example, with reference to the accompanying drawings in which:

FIG. 5 is a graph of the intensity of the test lines on the test strips of FIG. 4.

Figure 1:
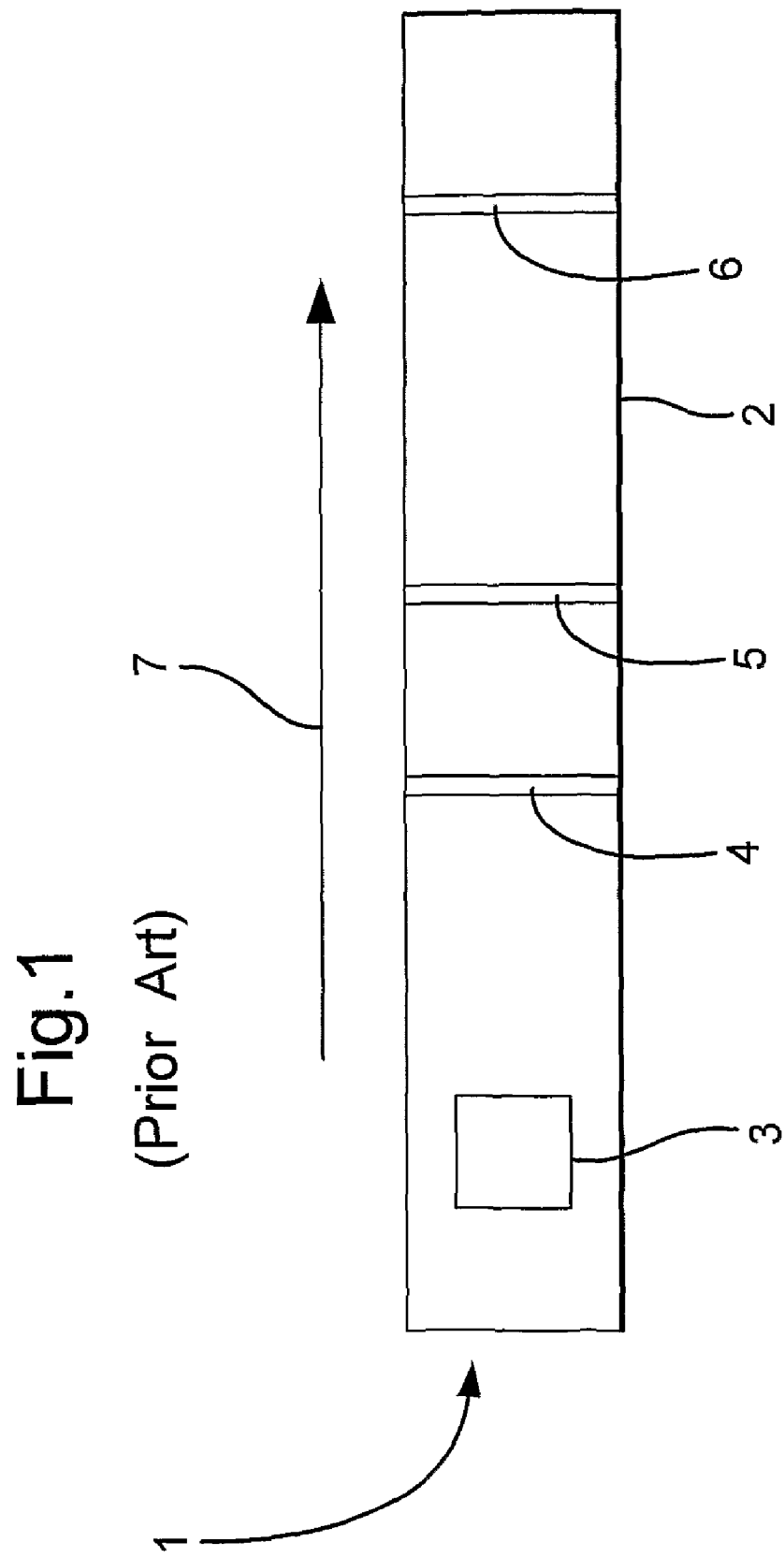
FIG. 1 is an illustration of a lateral flow immunoassay which may be used in accordance with one embodiment of the present invention.

As has previously been described in relation to FIG. 1, the presence or absence of the analyte hCG in a sample may be determined by using the lateral flow immunoassay kit 1 shown in FIG. 1.

In one embodiment of the present invention, a sample is provided in which it is desired to determine whether or not an active protease enzyme is present. The sample is pre-mixed with hCG. The hCG can be obtained from any source and may, for example, be recombinant in origin. After mixing of the hCG with the sample, the mixture is placed on the sample receiving zone 3 of the lateral flow diagnostic kit 1. The action of the lateral flow diagnostic kit then proceeds as has been explained above. It is to be appreciated that, since hCG has been added to the sample, the kit 1 will, by default, produce a line at the capture antibody band 5.

However, if the sample contains a protease which is capable of hydrolyzing hCG then the hCG is broken down into one or more degradation products and a line does not form at the capture antibody band 5. This is because the proteolysis of the hCG results either in the labelled antibody and the capture antibody failing to bind to the degradation products (because the epitope to which they bind is longer present) or the antibodies bind to separate epitopes which are no longer connected with each other because of degradation of other parts of the hCG analyte. In either case, the bridge or link that is provided by the hCG is not present and thus the labelled antibodies pass through the capture antibody band 5.

In practice, a protease may not completely degrade all hCG and some may remain intact. In these circumstances, a line forms at the capture antibody band 5 but it is of reduced intensity compared with the complete absence of protease control.

In any case, the absence of a visible line at the capture antibody band, or the presence of a line at the capture antibody band 5 with a reduced intensity, is indicative of the presence of a protease in the sample.

In one embodiment of the present invention, a kit is provided comprising a lateral flow immunoassay kit 1 as described above and a vessel containing hCG in isolated form (i.e. in pure form and without any contaminants). The kit would be used for mixing the sample in the vessel with the hCG and then depositing the mixture on the sample receiving zone 3. The assay then proceeds as described above.

It is very important to note that, in the above described embodiments, hCG is provided as simply one example of an analyte which may be used in the present invention. In other embodiments, different proteinaceous analytes are used. The analytes must be sensitive to protease activity. If a different analyte is used then the monoclonal antibodies in the labelled antibody band 4 and the capture antibody band 5 must be substituted for monoclonal antibodies specific for the different analyte. It is also to be noted that the two sets of monoclonal antibodies should be specific for different epitopes on the analyte so as to ensure that the analyte can perform the bridge or linking function.

It is also to be noted that in other embodiments of the present invention, a different label from a gold particle is provided. For example, in some embodiments, a fluorophore or chromophore is provided as the label. The fluorophore is visualised under ultra violet light. In some other embodiments, latex is provided as the label.

In some alternative embodiments, instead of the monoclonal antibodies in the labelled antibody band and the capture antibody band being specific for the whole analyte, the antibodies are instead specific for the degradation products of the analyte. More specifically, the monoclonal antibodies in the labelled antibody band 4 and the capture antibody band 5 are unable to bind the whole analyte but can instead bind epitopes which are revealed after proteolytic degradation of the analyte. Nevertheless, in these embodiments, the two epitopes to which the two sets of monoclonal antibodies bind must be present on a single degradation fragment. For example, if an analyte is hydrolyzed into three separate peptides by the activity of protease then the epitope to which the labelled antibody is specific and the epitope to which the capture antibody is specific must be on the same one of those three fragments. In this way, the single degradation fragment provides the bridge or linking function between the labelled antibody and the capture antibody.

In some embodiments, the sample is mixed with a protease inhibitor after mixing with the analyte. These embodiments thus ensure that, after proteolytic degradation of the analyte, the proteases are inactivated and so do not cleave the labelled or capture antibodies on the strip 2.

It is to be understood that it is not essential to the invention that the mixture of the sample and the protease are tested on a lateral flow diagnostic kit. In some alternative embodiments, for example, the mixture is instead tested on a flow-through immunoassay. A flow-through immunoassay comprises a substrate, such as a nitrocellulose sheet, onto which the antibodies of the capture antibody band of the previous embodiments are immobilised. Subsequently, the mixture of the sample and the analyte is added to the substrate and unbound sample and analyte is washed off. Labelled antibody is then deposited on the substrate, which binds to any analyte which is present on the substrate. Thus, in the presence of analyte to which the two antibodies are specific, the labelled antibody is bound to the substrate via the analyte and the immobilised capture antibody.

Accordingly, if a protease is present in the sample then the analyte is cleaved and, in the absence of an appropriate analyte, the labelled antibody is washed off. Alternatively, if a protease is not present in the sample then the analyte remains intact and the presence of the intact analyte is detectable when the labelled antibody is visualised on the substrate of the final step.

In further embodiments of the present invention, other binding assays are used instead.

In some embodiments of the present invention, the analyte is selected so as to be sensitive to a specific protease. For example, in one embodiment, a protease which hydrolyzes only at a specific amino acid residue sequence is detected. In order to detect this protease, an analyte is provided which comprises first and second epitopes which are connected by a linker sequence having the specific amino acid residue sequence. The labelled antibodies are specific for the first epitope; the capture antibodies are specific to the second epitope. Thus, in the presence of this specific protease, the analyte is cleaved and its presence may thus be detected in a subsequent immunoassay.

While the above described embodiments of the invention comprise antibodies to bind the analyte (i.e. they are immunoassays) this is not essential to the invention and the antibodies may be substituted for other types of binding components in alternative embodiments. For example, in one embodiment, the binding components are lectin proteins which bind to carbohydrate moieties present on the analyte.

EXAMPLES

Example 1

Figure 2:
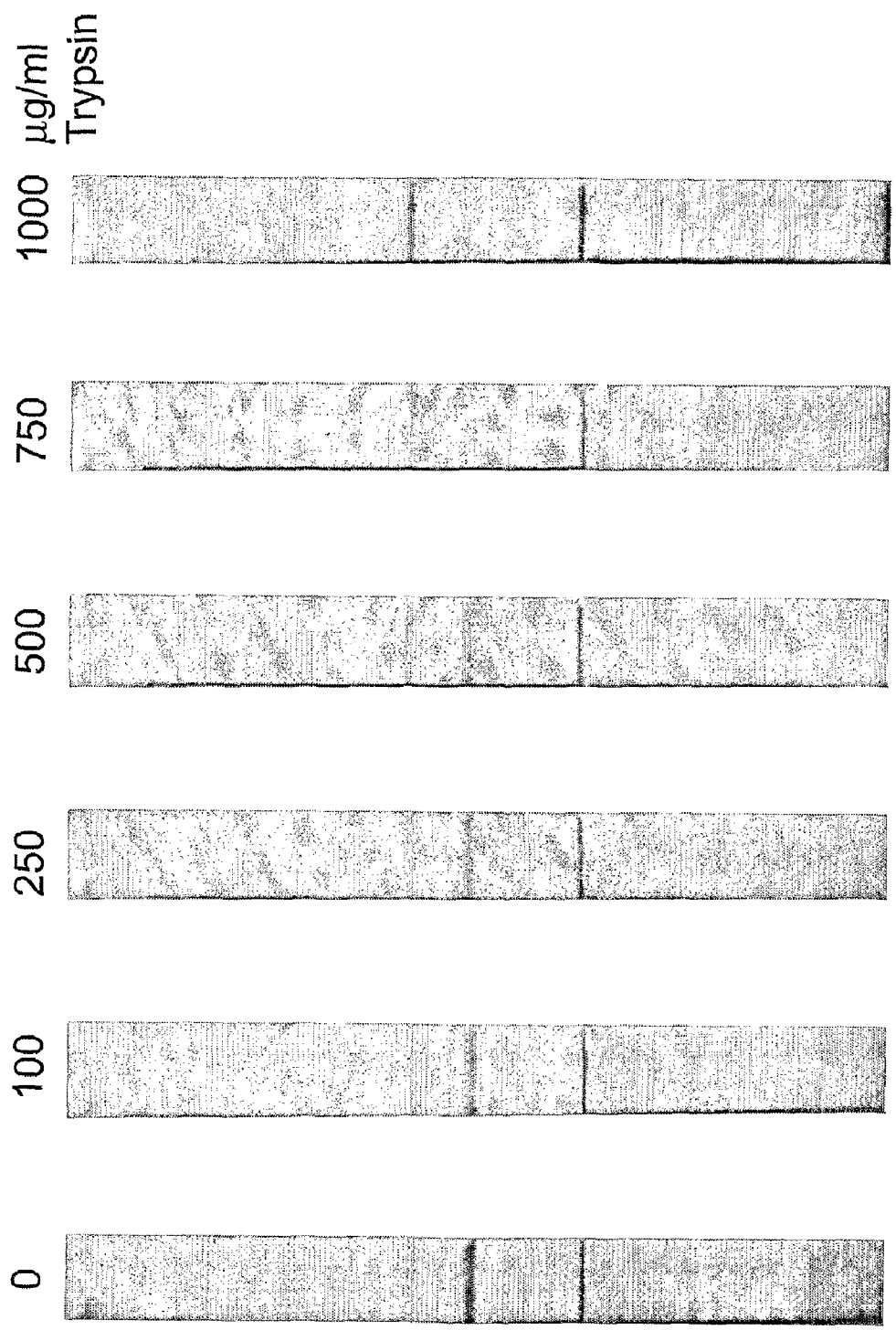
FIG. 2 is an image of a series test strips on which one embodiment of a method of the invention has been carried out.
Figure 3:
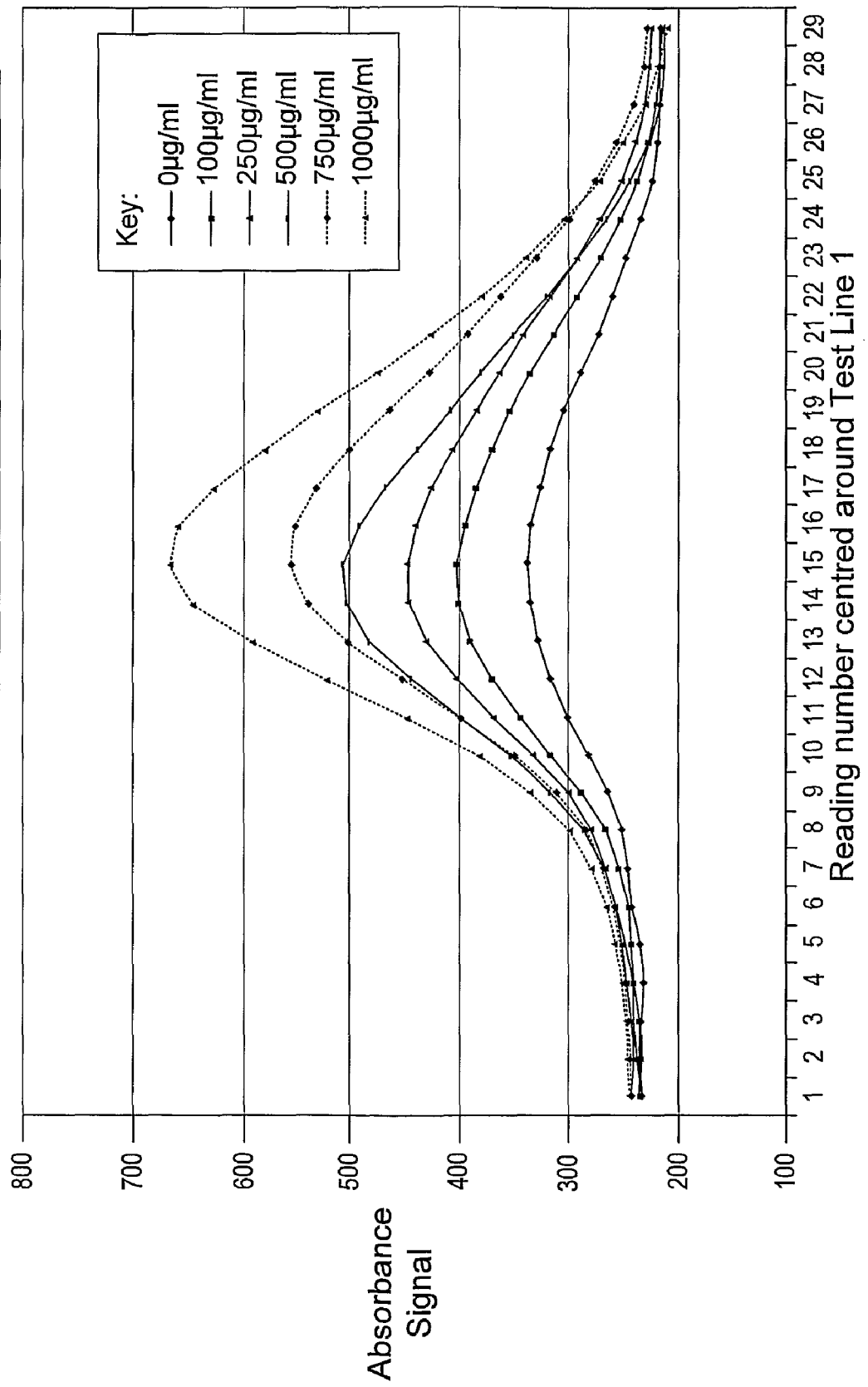
FIG. 3 is a graph of the intensity of the test lines on the test strips of FIG. 2.

The Use of hCG as the Degradable Analyte and Antibodies to Binding Cleavage Products for a Trypsin Assay Using a pregnancy test strip the following assay was performed for detection of Trypsin activity in a sample:
a) 130 µl of 2.5 IU/ml hCG stock analyte was mixed with 40 µl of Trypsin sample and incubated for 15 minutes at room temperature.
b) The above mixture prepared in (a) was added to base of pregnancy test strip held vertically on a support and allowed to chromatograph up the strip.
c) When all mixture prepared in (a) had soaked into the strip a 50 µl buffer wash (0.01 M PBS buffer, pH 7.4) was added to the base of the strip and allowed to chromatograph up the strip. A digital image of the test strips was taken and is shown in FIG. 2.
d) Strips were transferred to a reading system to analyse the absorbance profiles for developed test line. The reader was a scanning based system which scans a 12 mm length of a lateral flow test strip which contains the test lines of interest. Suspended above the test strip is a green LED and below the test strip is a photo-detector with which the software determines the absorbance of the strip. The reader took a reading every 100 µs during the scan. A graph of the results is shown in FIG. 3 in which an increase in line intensity corresponds to an increase in peak height.

Example 2

Figure 4:
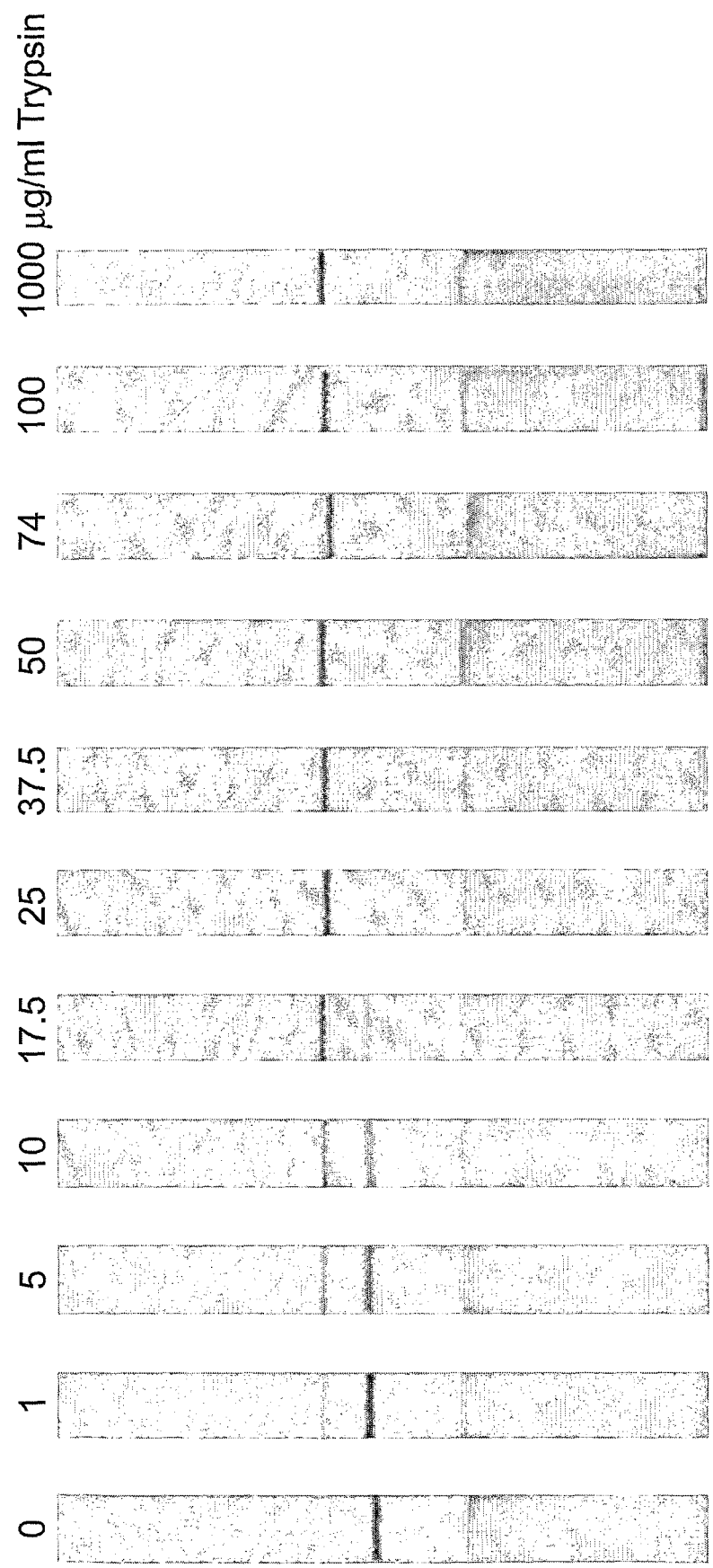
FIG. 4 is an image of a series test strips on which another embodiment of a method of the invention has been carried out.

The Use of Peptide as a Degradable Analyte and Biotin/Avidin to Bind the Cleavage Product for a Trypsin Assay Using an immunoassay test strip containing a streptavidin test line and an anti-mouse antibody control line the following assay was performed for detection of Trypsin activity in a sample:
a) 4 µl of 0.65 µg/ml peptide (Fluorescein-Val-Arg-Gly-[PEG]20-Biotin) was mixed with 3 µl of Trypsin sample and incubated for 5 minutes at room temperature.
b) The above mixture prepared in (a) was further mixed with 1.5 µl of anti-FITC gold conjugate, 13.5 µl BSA and 67 µl PBS and added to the base of the strip held vertically on a support and allowed to chromatograph up the strip.
c) When all mixture prepared in (b) had soaked into the strip a 150 µl buffer wash (0.01M PBS buffer, pH 7.4) was added to the base of the strip and allowed to chromatograph up the strip. A digital image of the test strips was taken and is shown in FIG. 4.
d) Strips were transferred to a reading system (as in Example 1) to analyse the absorbance profiles for the developed test line. A graph of the results is shown in FIG. 5 in which an increase in line intensity corresponds to an increase in peak height.

The invention claimed is:

1. A method of detecting a protease in a sample comprising the steps of:
   (i) providing an unlabelled protein analyte degradable by the protease;
   (ii) contacting the analyte with the sample;
   (iii) contacting the analyte with a specific labelling component such that the labelling component specifically binds to the analyte, wherein the labelling component is associated with a label;
   (iv) capturing the analyte with a specific capture component such that, if intact, the analyte acts as a link between the labelling component and the capture component; and
   (v) detecting the presence of the label associated with the capture component, wherein the absence of a detectable label or detection of a reduced label intensity at the location at which the capture component is immobilised is indicative of the presence of a protease in the sample.

2. The method according to claim 1, wherein steps (iii) and (iv) are part of a lateral flow assay.

3. The method according to claim 1, wherein the specific labelling component comprises an antibody or an antigen binding fragment thereof.

4. The method according to claim 1, wherein the specific capture component comprises an antibody or an antigen binding fragment thereof.

5. The method according to claim 1, wherein the analyte is hCG.

6. The method according to claim 1, wherein the specific labelling component and the specific capture component are located on different portions of a liquid flow path.

7. The method according to claim 1, wherein the specific capture component is located on a solid substrate.

8. The method according to claim 7, wherein the specific capture component is immobilised on the solid substrate.

* * * * *